(12) United States Patent
Krieg et al.

(10) Patent No.: US 6,509,537 B1
(45) Date of Patent: Jan. 21, 2003

(54) METHOD AND DEVICE FOR DETECTING AND DIFFERENTIATING BETWEEN CONTAMINATIONS AND ACCEPTS AS WELL AS BETWEEN DIFFERENT COLORS IN SOLID PARTICLES

(75) Inventors: Gunther Krieg, Im Rennich 12, D-76227 Karlsruhe (DE); Dirk Fey, Karlsruhe (DE); Jürgen Bohleber, Bühl (DE); Manfred Dausch, Göcklingen (DE)

(73) Assignee: Gunther Krieg, Karlsruhe (DE)

( * ) Notice: Subject to any disclaimer, the term of this patent is extended or adjusted under 35 U.S.C. 154(b) by 0 days.

(21) Appl. No.: 09/743,517

(22) PCT Filed: May 14, 1999

(86) PCT No.: PCT/EP99/03325
§ 371 (c)(1),
(2), (4) Date: Jan. 11, 2001

(87) PCT Pub. No.: WO00/70331
PCT Pub. Date: Nov. 23, 2000

(51) Int. Cl.⁷ .............................. B07C 5/00; B07C 5/342
(52) U.S. Cl. ........................ 209/579; 209/585; 209/587
(58) Field of Search ................................. 209/579, 585, 209/587; 356/73, 337, 340, 342, 343

(56) References Cited

U.S. PATENT DOCUMENTS

| | | | |
|---|---|---|---|
| 2,750,519 A | * | 6/1956 | Summerhayes, Jr. et al. ..................... 250/214 |
| 4,231,661 A | * | 11/1980 | Walsh et al. ................. 356/340 |
| 4,600,105 A | | 7/1986 | Van Zyl |
| 4,636,074 A | | 1/1987 | Levy |
| 4,976,540 A | * | 12/1990 | Kitamura et al. .............. 356/38 |
| 5,813,543 A | * | 9/1998 | Gesing et al. .............. 209/653 |
| 5,862,919 A | * | 1/1999 | Eason ......................... 209/577 |
| 6,060,677 A | * | 5/2000 | Ulrichsen et al. ........... 209/577 |

FOREIGN PATENT DOCUMENTS

| | | |
|---|---|---|
| EP | 0 345 949 | 12/1989 |
| WO | WO 93 11 403 | 6/1993 |
| WO | WO 96 06 689 | 3/1996 |
| WO | WO 98 33 058 | 7/1998 |

* cited by examiner

Primary Examiner—Donald P. Walsh
Assistant Examiner—Mark J. Beauchaine
(74) Attorney, Agent, or Firm—Paul Vincent

(57) ABSTRACT

The invention concerns a method and a device for detection of and differentiation between base materials, colors and contamination in granulate-like or tablet-shaped substances, characterized in that the substances are illuminated in a linear manner with a laser beam, the optical radiation re-emitted by the substances is spectroscopically analyzed, and the substances are classified and sorted into different groups.

24 Claims, 11 Drawing Sheets

METHOD AND DEVICE FOR DETECTING AND DIFFERENTIATING BETWEEN CONTAMINATIONS AND ACCEPTS AS WELL AS BETWEEN DIFFERENT COLORS IN SOLID PARTICLES

BACKGROUND OF THE INVENTION

Product quality or color control is an essential quality criterion in many technical on-line processes. The production of plastic containers, in particular plastic bottles for the beverage industry, using granulated recycled material, requires separation and sorting of different color portions, different plastic types, e.g. polyethylene, polyamide, polyvynylchloride, the recognition and sorting of e.g. fractions contaminated with gasoline, diesel, benzene, toluene, xylene, to enable re-use e.g. in the food industry. To achieve this object, the reusable pure base materials must be differentiated and separated from the contaminated granulates and moreover, the fragments having different colors must be sorted to obtain portions of pure color.

Prior art methods and devices unsatisfactorily achieve this complex object to a limited extent only. Devices are known which permit recognition of color with subsequent color sorting by controlled air flow nozzles and using CCD color cameras. These systems are disadvantageous in that the measuring speed is unacceptably slow and the signal-to-noise ratios too low, and are therefore not suitable for use in the present technical process. Moreover, methods for identifying and separating different plastic materials have been developed. The methods used thereby are not suited for use with granulates or granulate-similar portions of recycled materials, since the intended identification and sorting of smaller or larger bottles, containers etc. requires 1000 times faster measuring speeds to cope with the minimum mass flow required for economic reasons. A further drawback consists in that the detection of colors and the differentiation of materials require separate systems using different physical principles, i.e. CCD cameras for detecting the color or NIR absorption for plastic classification, wherein the total cost per system is above the economically justifiable level. The largest drawback is the fact that none of the above-mentioned methods allows proof of contamination by foreign matter deposited in the base material. The latter is absolutely required e.g. within the scope of recycling plastic material used in connection with food, which is to be used a plurality of times as food containers.

It is therefore the underlying purpose and object of the present invention to propose a novel method or devices which not only enable identification of color and classification of material but also identification of contamination in the base material, wherein, for economic reasons, the three problems shall be solved simultaneously using only one single basic physical principle.

SUMMARY OF THE INVENTION

The present invention solves these three problems in that the recycling granulate, which is transported on a conveyor belt, is illuminated by a laser beam and the radiation re-emitted by the granulate is spectroscopically analyzed within a broad spectral range. The invention additionally provides means for extensive detection and evaluation of the spectra to determine the colors of the base materials and the contamination of the granulates, in real time. The invention is explained in more detail below in FIGS. 1 through 9.

DESCRIPTION OF THE PREFERRED EMBODIMENT

Figure 1:
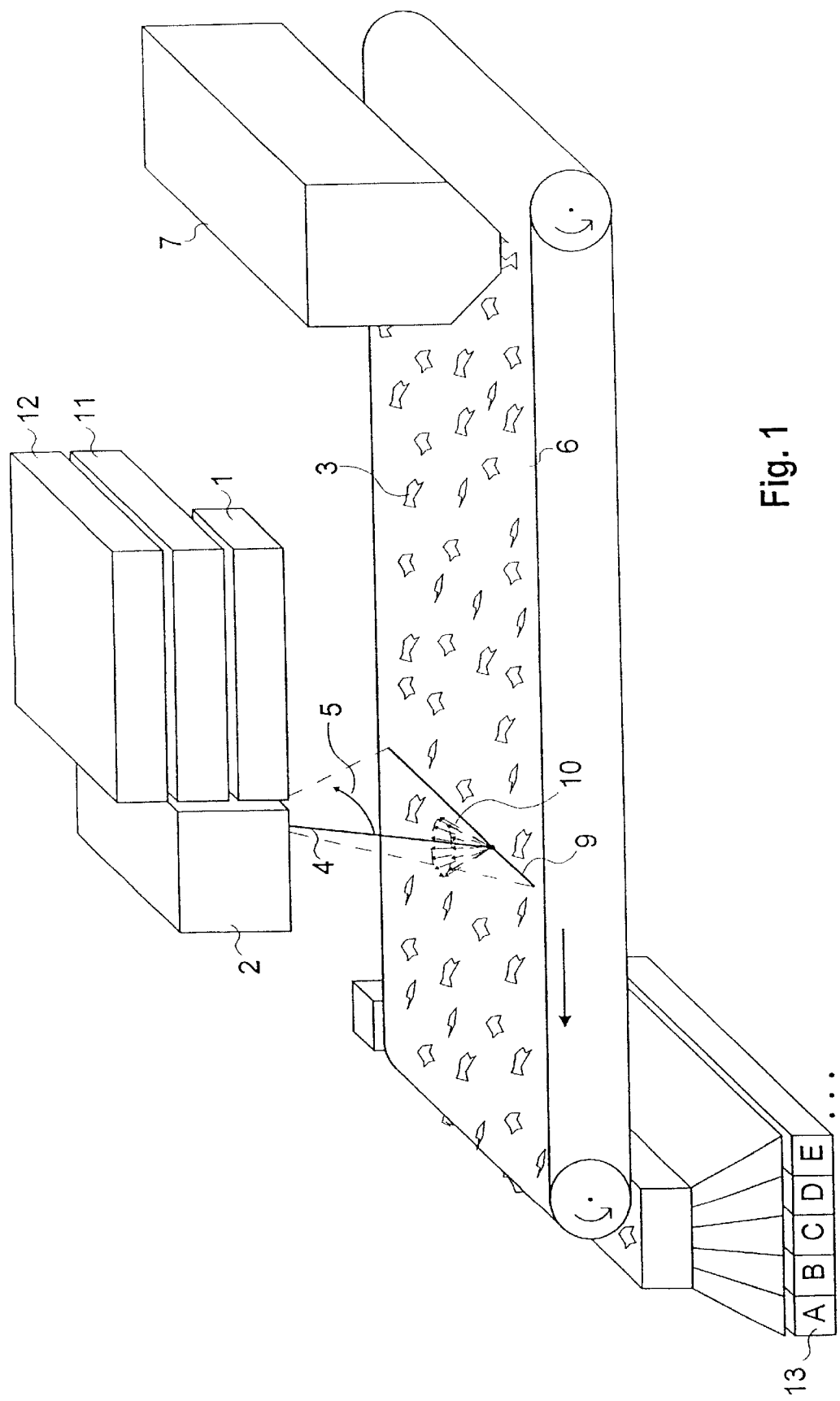
FIG. 1 shows the basic construction of the overall system for on-line detection and sorting of contaminated granulates or tablets of different colors and different base materials.
Figure 2:
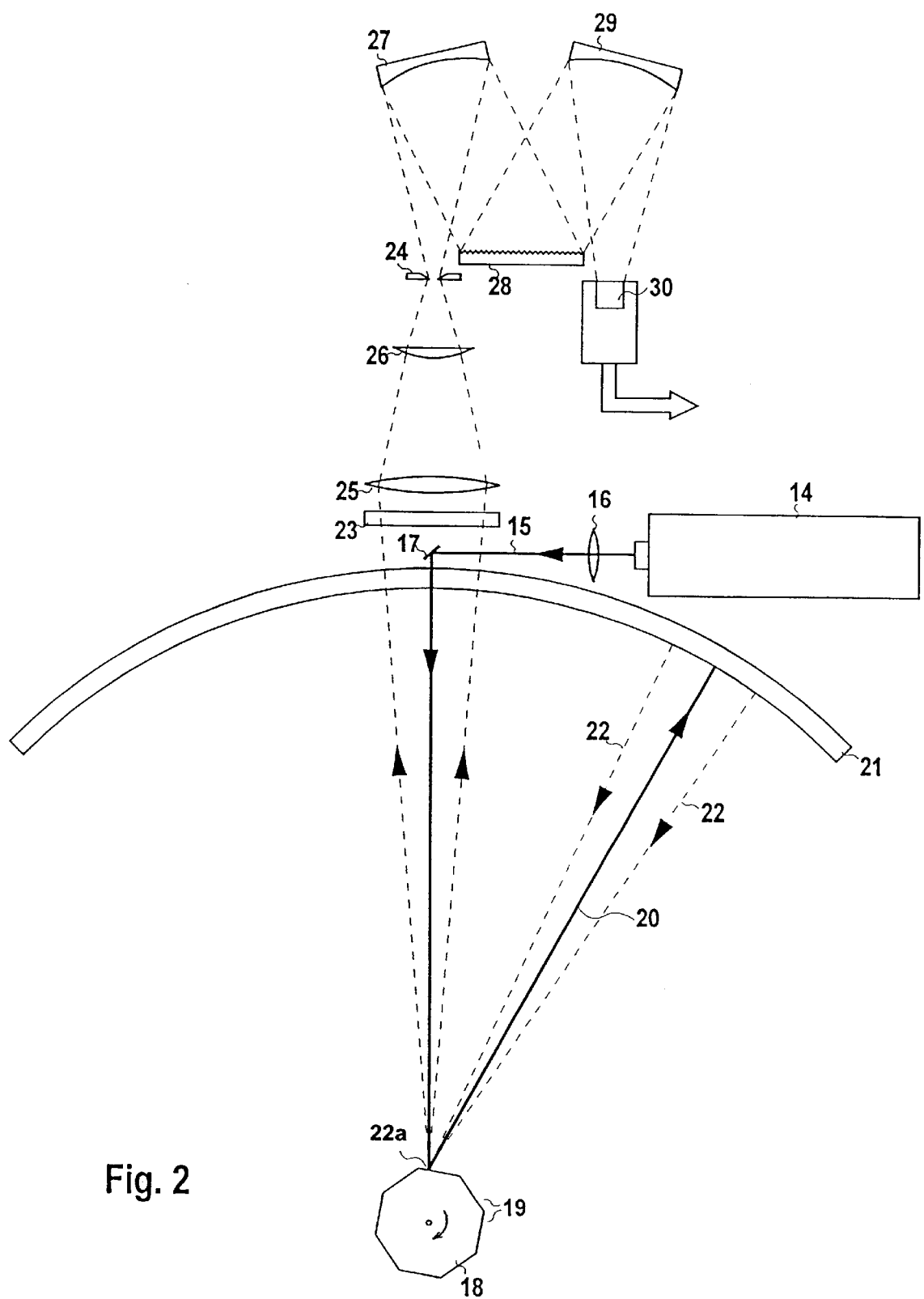
FIG. 2 shows the optical arrangement for illumination of the measuring material and for detection of the radiation re-emitted by the measuring material using a polygonal mirror wheel and a toroidal mirror.
Figure 3:
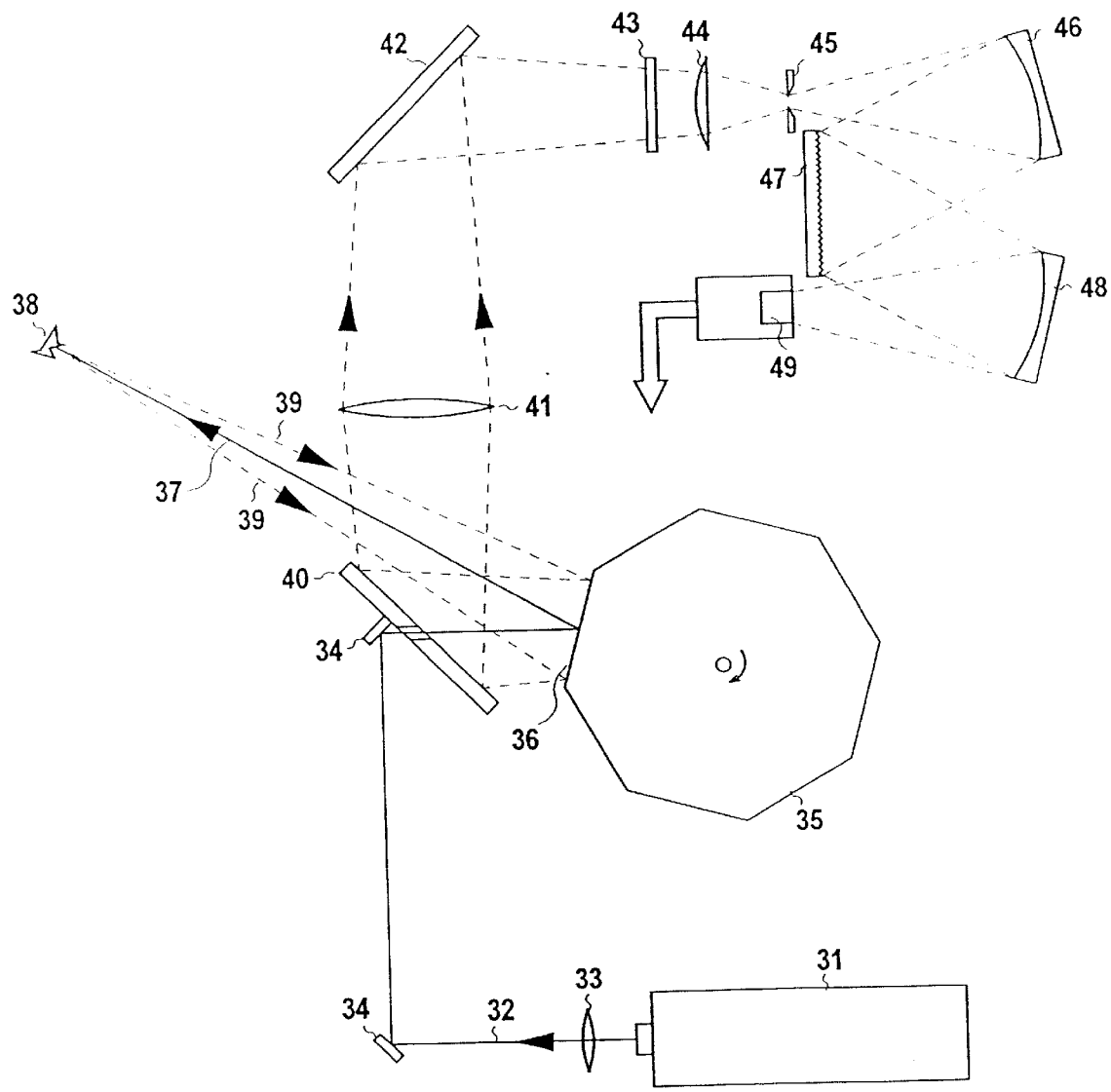
FIG. 3 shows the optical arrangement for illumination of the measuring material and for detection of the radiation re-emitted by the measuring material via a polygonal mirror wheel only.

In accordance with FIG. 1, a laser (4) beam is guided over the measuring material (3) in a linear manner using an optical system (2) (further described in FIG. 2 or FIG. 3). The laser beam (4) scans the entire angular range (5) for detecting the entire width of the conveyor belt (6) which is supplied with granulate material (3) via a silo (7) or with tablets or other test material via a feed device (not shown in detail). Illumination of test samples (3) is effected point-by-point (9) through cycling of the laser light. Linear scanning is also feasible through use of a continuously radiating laser (1). The secondary light (10) generated through scattering, fluorescence, Raman laser radiation, reflection and other optical re-emission effects is detected by the optical system (2) in a wide angular region and supplied to a spectrometer (11) whose signals are processed by an evaluation unit (12), exemplarily illustrated in FIG. 6. Following classification of the test samples (3) into individual color classes, separate material classes and contaminants, they are sorted via a conventional separation system (e.g. via cycled nozzles) into different separate portions (13) which can be transported in this form to another production process or, if contaminated, to a disposal system.

FIG. 2 shows the laser (14) whose beam (15) is incident on a polygonal wheel (18) after collimation by a lens (16) and deflection via a reflector (17). The end surfaces (19) of the polygonal wheel (18) rotate at a high angular velocity and are formed as mirrors to azimuthally guide the laser beam (20), in a temporal saw tooth manner, over the three-dimensional concave toroidal mirror (21) to effect linear laser beam scanning (9) of the test material (3) on the conveyor belt (6) of FIG. 1. The divergent re-emitted light (10) (see FIG. 1) is also collected by the toroidal mirror (21), transformed into a converging bundle of rays (22) and reflected at the point (22a) (where the laser impinges) to gain access to the spectrometer (11), shown in the upper part of FIG. 1. An optical filter (23) is provided at the entrance of the spectrometer which removes stray light coming from laser radiation (14) which is reflected e.g. on the surfaces of optical components such as eg. the lens (16) and which would otherwise gain indirect access to the spectrometer. The optical filter (23) is designed to suppress the emission wavelengths of the laser (14) which are preferably at emission wavelengths of the YAG laser, i.e. at 1046 nm and their frequency-multiple wavelengths of 523 nm, 349 nm, and 262 nm. The light focused, by means of the lenses (25,26), on the gap (24) of the spectrometer is incident, via a first concave mirror (27), on the optical grid (28) which decomposes the spectrum of optical radiation into its wavelength components and projects same, in dependence on the wavelength and via a second concave mirror (29), onto the sensor system (30). The sensor system (30) consists e.g. of a linear CCD array. Depending on the spectral range to be examined, linear arrays of Si photodiodes or Si photoelements or corresponding arrangements of In Ga As can alternatively be used. FIG. 6 shows, in more detail, a specially formed sensor system arrangement using photomultiplier arrays.

FIG. 3 shows the laser (31), whose beam (32) is incident on the mirror (36) of the polygonal wheel (35) following collimation by a lens (33) and deflection via the reflectors (34). The end surfaces (36) of the polygonal wheel (35) rotate at a high angular velocity and are formed as mirrors to azimuthally guide the laser beam (37), in temporal saw-tooth motion, directly onto the measuring material (38). In accordance with FIG. 1, this produces a linear laser beam scan (9) of the test material (3) on the conveyor belt (6). The diverging re-emitted light (10) (FIG. 1) is gathered by the mirror (36), and reflected to reach, via a lens (41) and mirror (42), the spectrometer (11) (upper part of FIG. 1). An optical filter (43) is provided at the entrance to the spectrometer to block stray light coming from the laser (31) radiation which is e.g. reflected on the surfaces of optical components such as e.g. the lens (33) and which would otherwise gain indirect entrance to the spectrometer. The optical filter (43) is therefore designed such that it suppresses the emission wavelengths of the laser (31). These are preferably at emission wavelengths of the YAG laser, i.e. at 1046 nm and their frequency-multiple wavelengths of 523 nm, 349 nm, and 262 nm.

The light focused by the lens (44) on the gap (45) of the spectrometer is initially reflected by a first concave mirror (46) onto the optical grid (47) which decomposes the spectrum of the optical radiation into its wavelength components and which images same, in dependence on the wavelength and via a second concave mirror (48), onto the sensor system (49). The sensor system (49) consists e.g. of a linear CCD array. Depending on the spectral range to be examined, linear arrays of Si photodiodes or Si photoelements or corresponding arrangements of In Ga As can be alternatively used. A specially designed sensor system arrangement using photomultiplier arrays is shown in more detail in FIG. 6.

Figure 4:
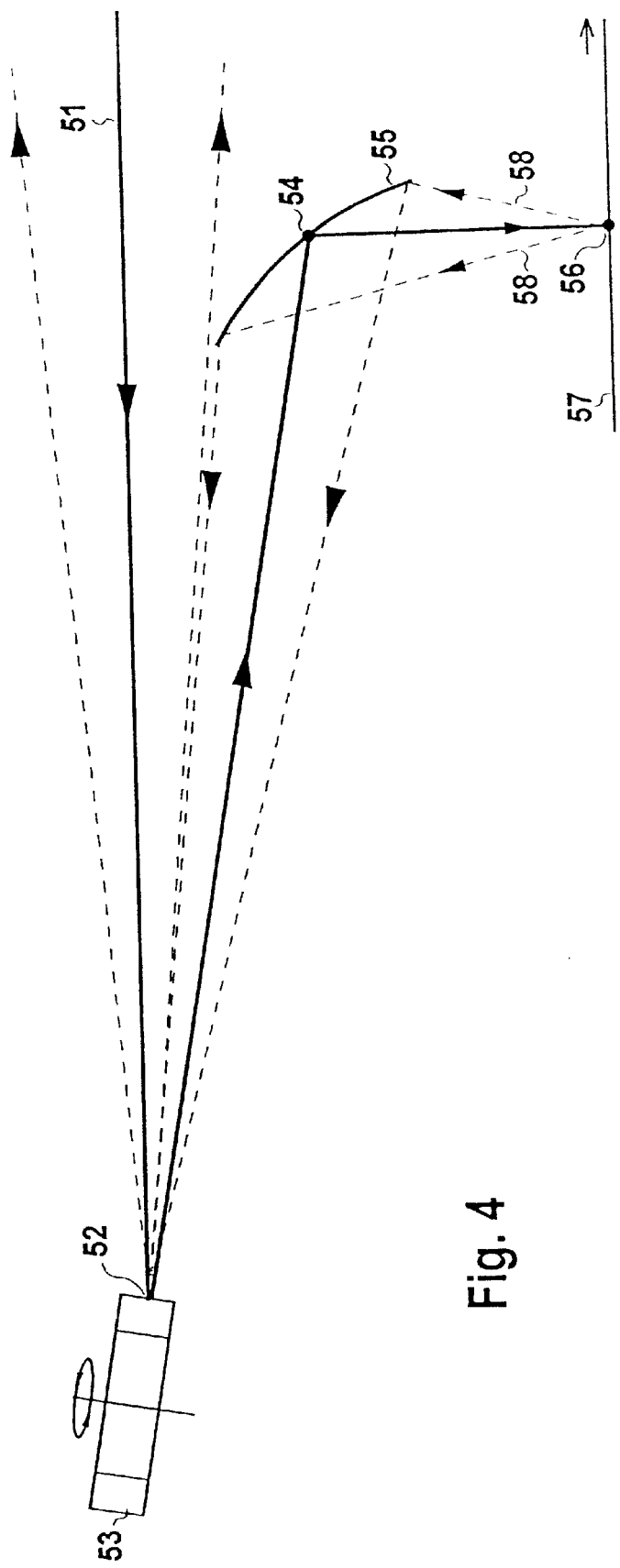
FIG. 4 shows a side view of an essential part of the optical arrangement shown in FIG. 2.
Figure 5:
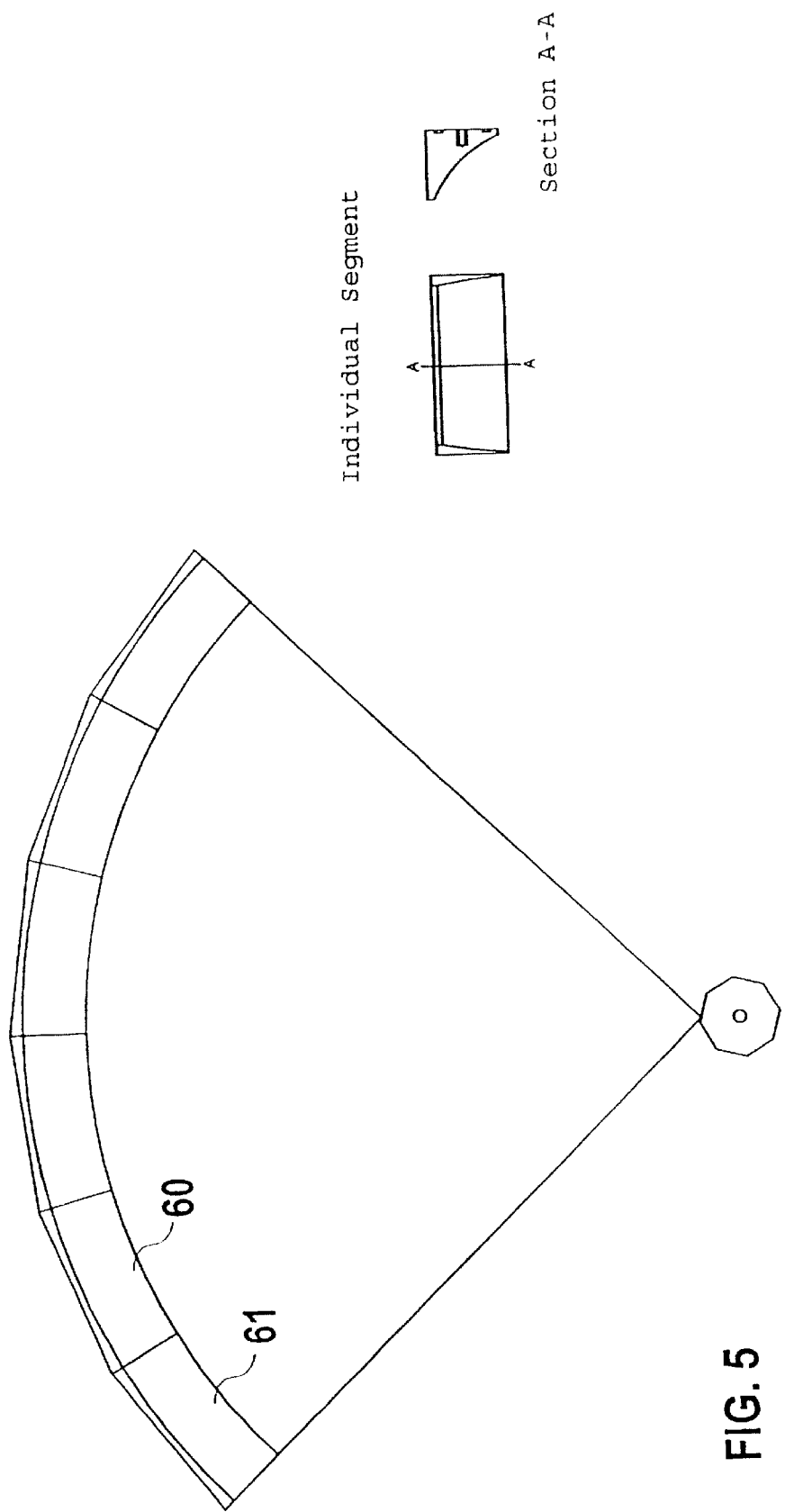
FIG. 5 shows the construction of the toroidal mirror used for radiation deflection.

FIG. 4 shows a side view of an essential part of the optical arrangement of FIG. 2, once more illustrating the laser beam (51) and its point of impingement (52) on the reflector surfaces of the polygonal wheel (53), its reflection (54) on the toroidal mirror (55) and its point of impingement (56) on the conveyor belt (57). The path of the rays (58) of the radiation re-emitted by the granulate or the respective tablet, which extends coaxially and opposite to the laser beam (51) is also shown. This special inventive optical path for the exciting laser beam (51) and for the re-emitted beam (58) is achieved, in particular, through the use of the toroidal mirror (55), having different radii of curvature in the sectional planes of FIGS. 2 and 4. To detect the required angular range of re-emitted radiation, a toroidal mirror is required having dimensions of approximately 1.5 m×0.3 m. For manufacturing reasons, the mirror is made from individual segments (60,61) (see FIG. 5).

Figure 6A:
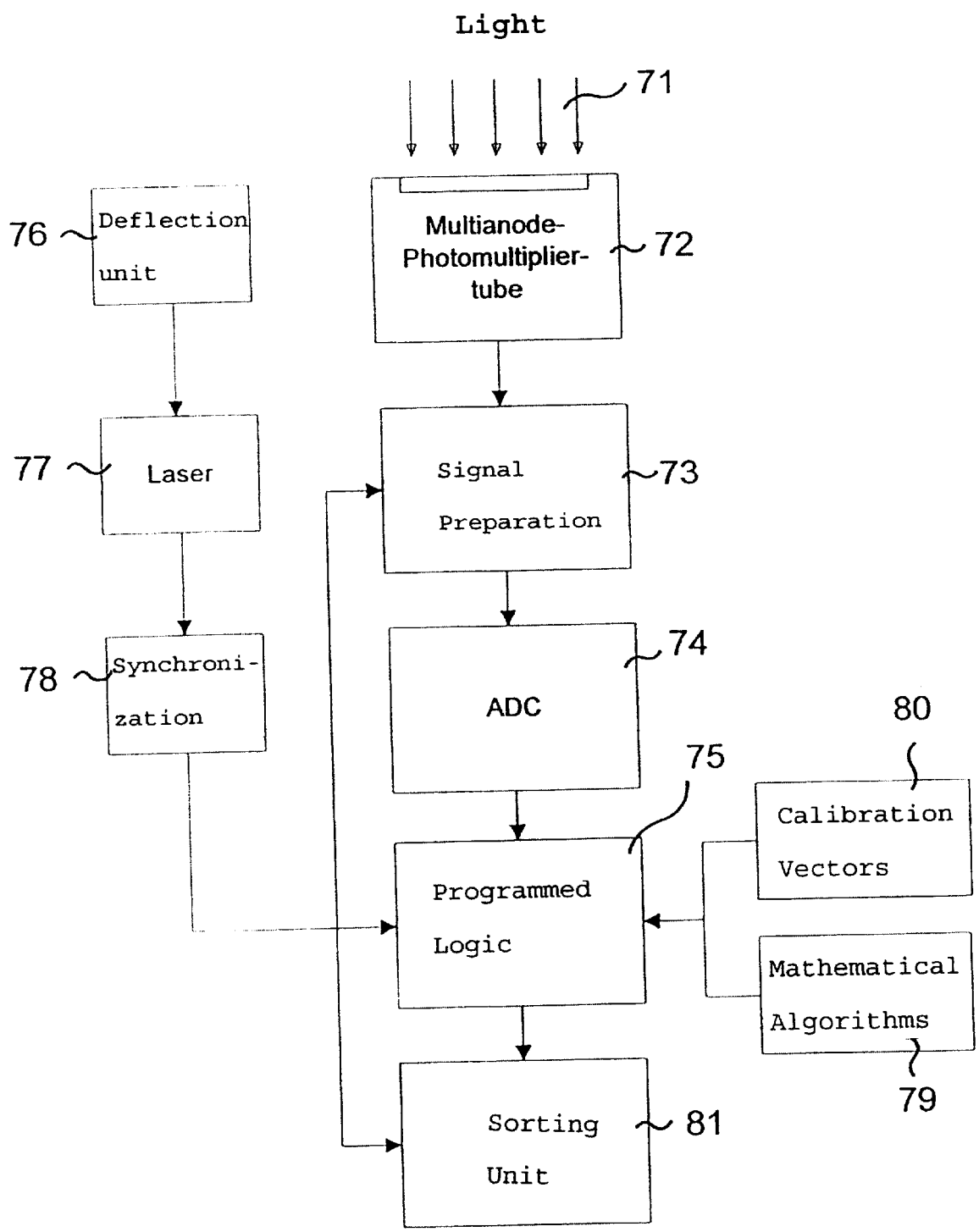
FIG. 6a shows a first selected arrangement of the sensor technology and signal processing for ultra-rapid evaluation of the optical signals.

In accordance with FIG. 6a, the spectrally decomposed light (71) is detected by a multi-anode photomultiplier tube (72). The respective spectrum reaches, via signal preparation (73) and an analog/digital converter (74), a programmed logic (75) which effects material identification, color determination and detection of contamination in synchronization with the optical deflection unit (76) of FIGS. 2, 3 and 4, the laser (77) and a special synchronization unit (78) and in cooperation with mathematical algorithms (79) and externally calculated calibration vectors (80) and passes respective commands to the sorting unit (81).

Figure 6B:
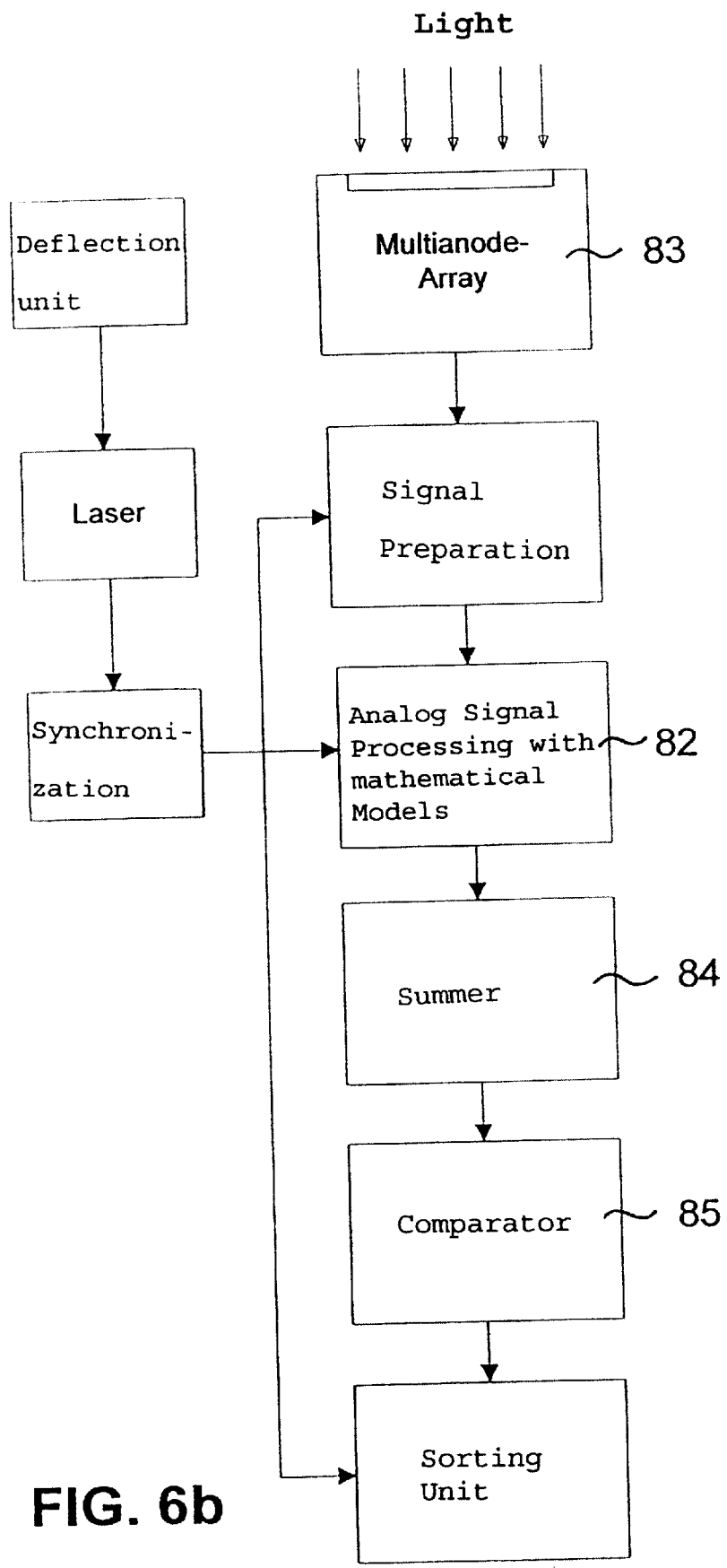
FIG. 6b shows a second selected arrangement of the sensor technology and signal processing for ultra-rapid evaluation of the optical signals.

FIG. 6b shows a further variant of the signal evaluation, wherein the programmed logic (75) in FIG. 6a is replaced by analog signal processing using mathematical models (82). The individual signal channels of the multi-anode photomultiplier tube (83) are processed in parallel via analog switching elements in accordance with a respectively pre-determined mathematical model. A downstream summer (84) adds the signal contents of all parallel channels into one single resulting signal which is classified by a comparator (85) into the following categories contamination or alternatively into the respective material class, including color.

Figure 6C:
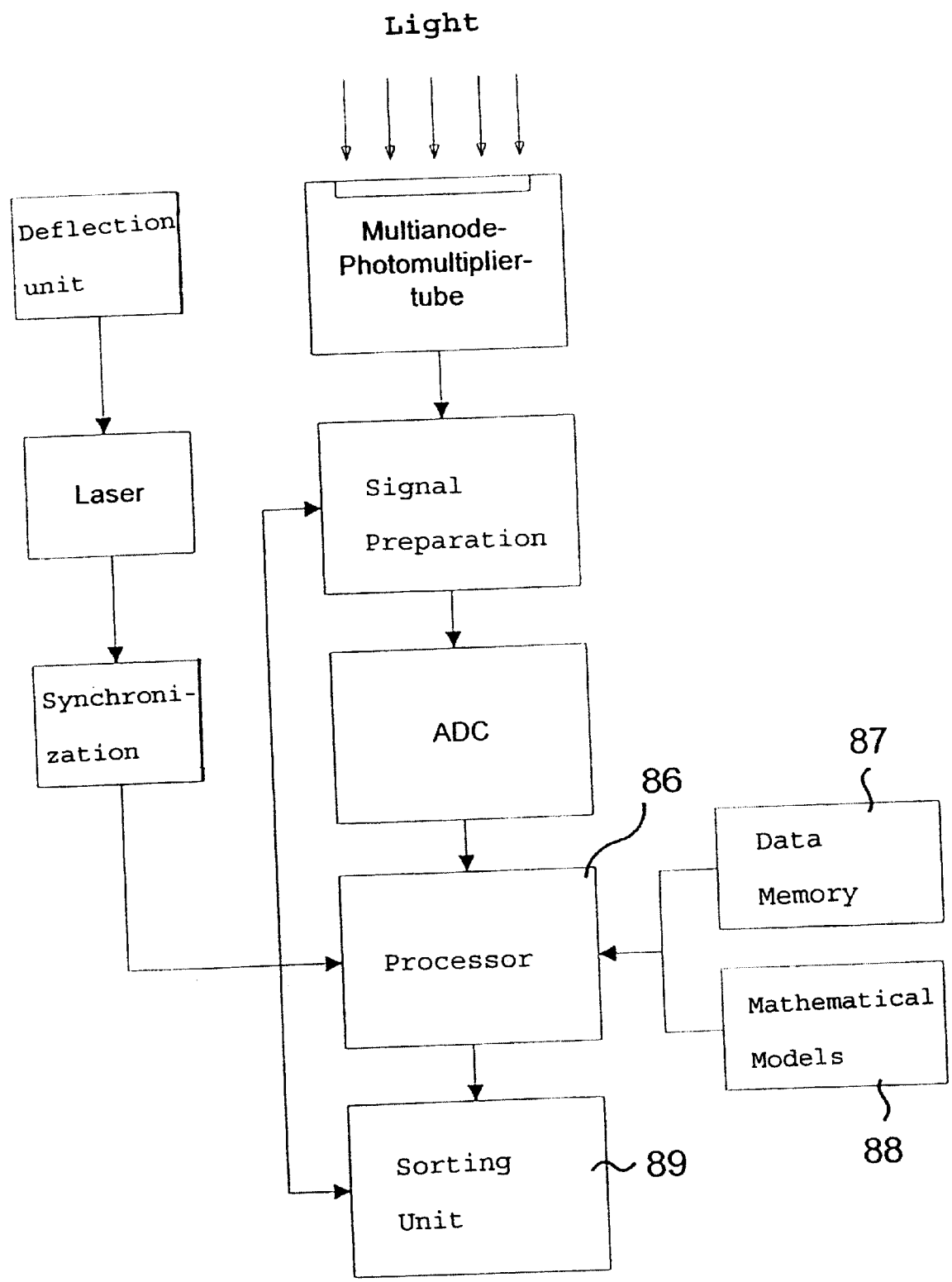
FIG. 6c shows a third selected arrangement of the sensor technology and signal processing for ultra-rapid evaluation of the optical signals determining contamination.

The third variant of the signal evaluation uses a processor (86) in accordance with FIG. 6c which compares the currently measured spectra with the reference spectra stored in a data memory (87), assesses them and passes corresponding commands on to the sorting unit (89). Alternatively or additionally, the respective current spectrum can be assessed and classified via mathematical models located in a memory (88).

Figure 7:
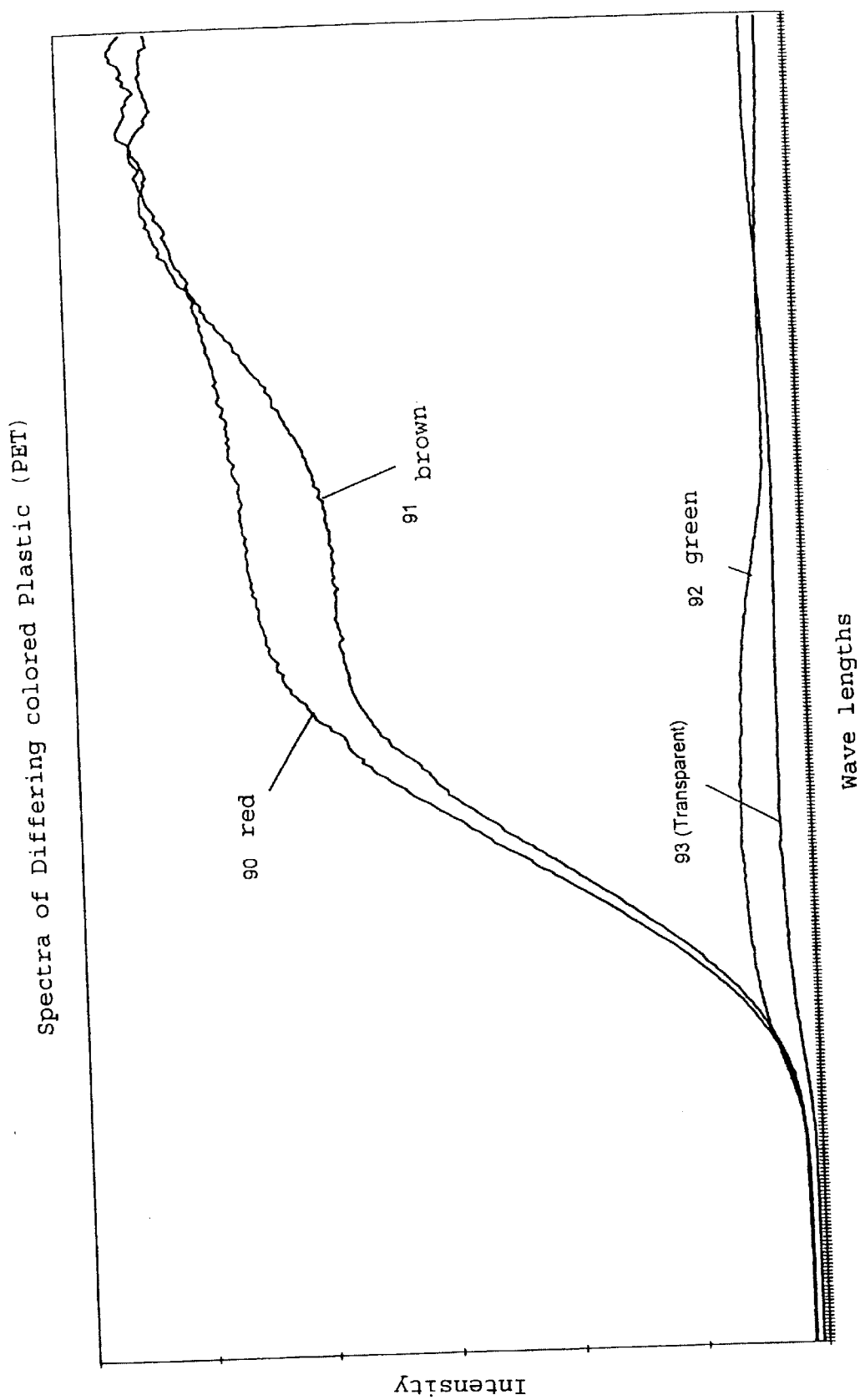
FIG. 7 shows an example of emission spectra for detecting and selecting the color.

FIG. 7 shows color detection according to the inventive method for differently colored PET materials in the form of different spectra for the colors red (90), brown (91), green (92) and transparent (93). One can see that clear color differentiation is possible.

Figure 8:
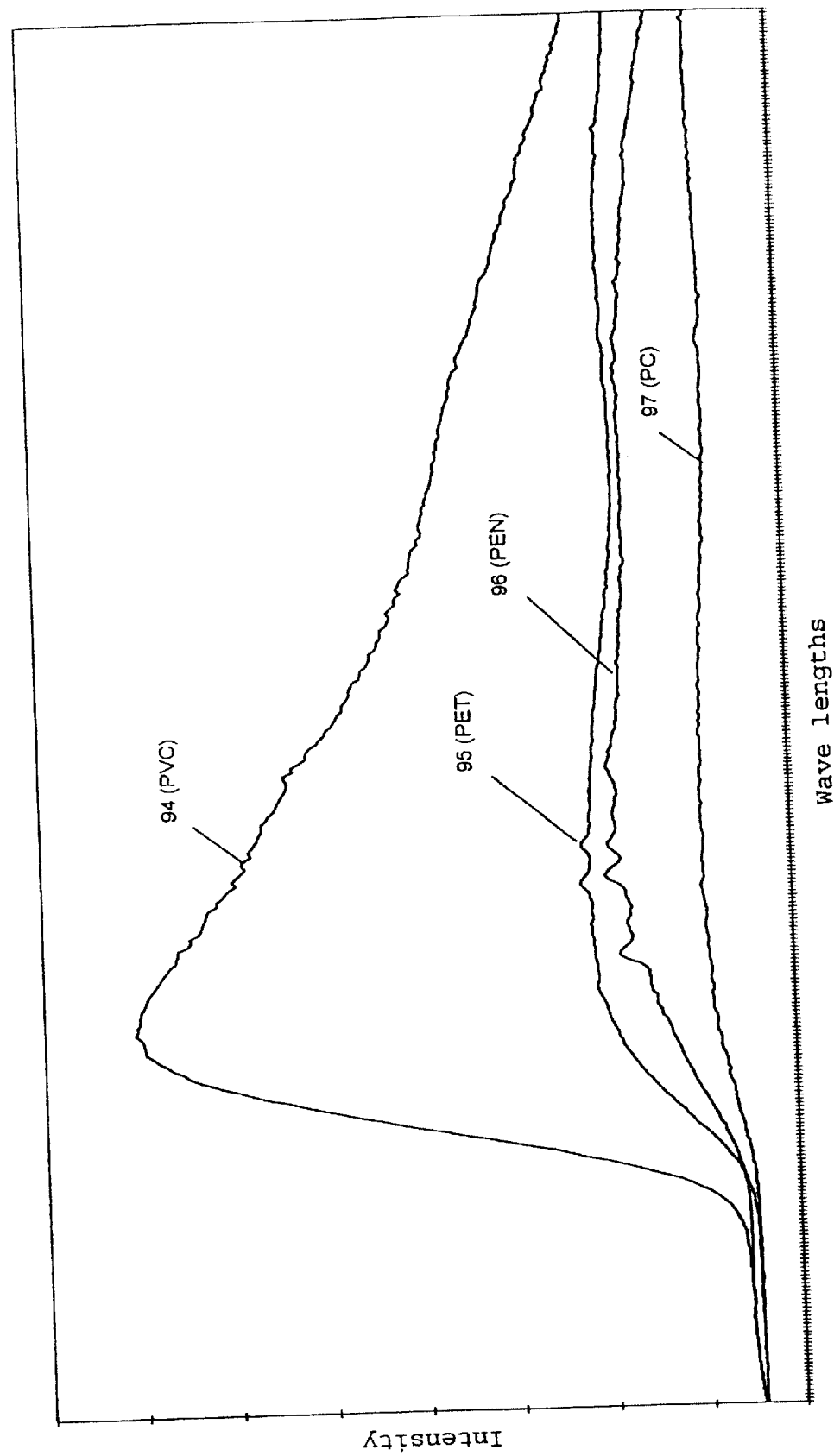
FIG. 8 shows an example of emission spectra for determining the material.

FIG. 8 combines the spectra of different materials with the base materials PVC (94), PET (95), PEN (96) and PC (97) which also differ with clearly distinguished characteristic curve shapes.

Figure 9:
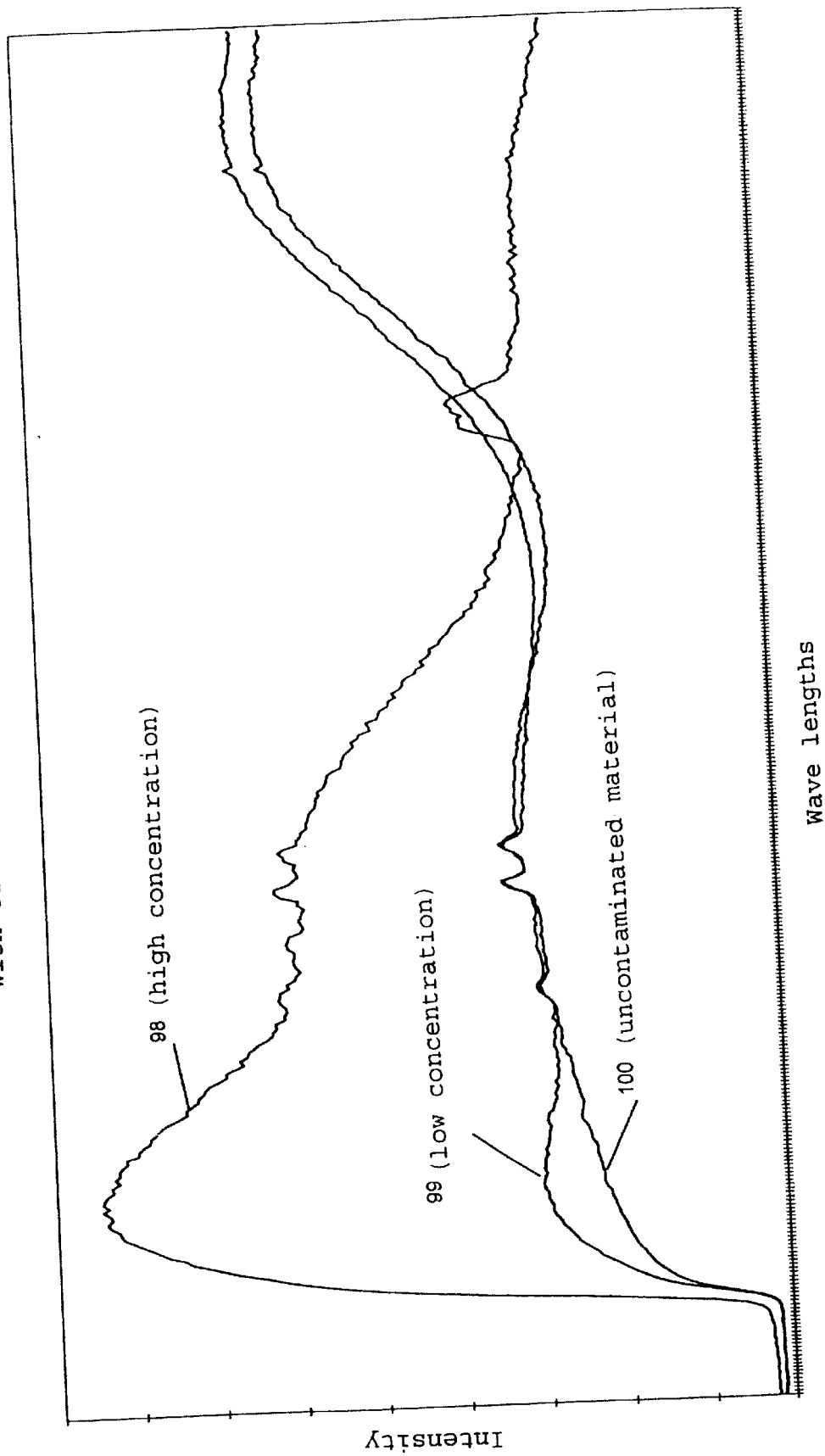
FIG. 9 shows an example of emission spectra for determining contamination.

The contamination spectra obtained according to the new method are shown in FIG. 9. Using the example of a cellulose lacquer diluent, the spectrum (98) shows a high contamination concentration, whereas the spectrum (99) shows a relatively low contamination concentration in the PET base material. In comparison therewith, the spectrum (100) shows the non-contaminated base material PET.

We claim:

1. A method of detecting and differentiating between base materials, colors and contamination in granulate-like or tablet-shaped substances, the method comprising the steps of:

a) linearly irradiating and exciting the substances with a laser;

b) detecting re-emitted secondary radiation from the substances;

c) spectroscopically analyzing said secondary radiation; and d) classifying and sorting the substances following step c), wherein step b) comprises detecting said re-emitted secondary radiation as a spectrum using a multi-anode photomultiplier tube, and step c) comprises effecting substance analysis, color determination and contaminant detection via signal preparation, programmed logic and mathematical algorithms including calibration vectors.

2. The method of claim 1, wherein said irradiating of the substances in step a) and said detecting of said re-emitted radiation in step b) are carried out via an optical arrangement comprising a reflecting polygonal wheel and a concave toroidal mirror.

3. The method of claim 2, wherein said concave toroidal mirror comprises several individual segments.

4. A method of detecting and differentiating between base materials, colors and contamination in granulate-like or tablet-shaped substances, the method comprising the steps of:
   a) linearly irradiating and exciting the substances with a laser;
   b) detecting re-emitted secondary radiation from the substances;
   c) spectroscopically analyzing said secondary radiation; and
   d) classifying and sorting the substances following step c),
   wherein step b) comprises detecting said re-emitted secondary radiation as a spectrum using a multi-anode photomultiplier tube, and step c) comprises effecting substance analysis, color determination and contaminant detection by preparing signals with analog multi-channel signal processing according to mathematical models, summing up of the contents of all signal channels, and classifying a summed signal.

5. The method of claim 4, wherein said irradiating of the substances in step a) and said detecting of said re-emitted radiation in step b) are carried out via an optical arrangement comprising a reflecting polygonal wheel and a concave toroidal mirror.

6. The method of claim 5, wherein said concave toroidal mirror comprises several individual segments.

7. A method of detecting and differentiating between base materials, colors and contamination in granulate-like or tablet-shaped substances, the method comprising the steps of:
   a) linearly irradiating and exciting the substances with a laser,
   b) detecting re-emitted secondary radiation from the substances;
   c) spectroscopically analyzing said secondary radiation; and
   d) classifying and sorting the substances following step c),
   wherein step b) comprises detecting said re-emitted secondary radiation as a spectrum using a multi-anode photomultiplier tube, and step c) comprises effecting substance analysis, color determination and contaminant detection via a processor having access to reference spectra contained in a data memory.

8. The method of claim 7, wherein said irradiating of the substances in step a) and said detecting of said re-emitted radiation in step b) are carried out via an optical arrangement comprising a reflecting polygonal wheel and a concave toroidal mirror.

9. The method of claim 8, wherein said concave toroidal mirror comprises several individual segments.

10. A method of detecting and differentiating between base materials, colors and contamination in granulate-like or tablet-shaped substances, the method comprising the steps of:
    a) linearly irradiating and exciting the substances with a laser,
    b) detecting re-emitted secondary radiation from the substances;
    c) spectroscopically analyzing said secondary radiation; and
    d) classifying and sorting the substances following step c),
    wherein step b) comprises detecting said re-emitted secondary radiation as a spectrum using a multi-anode photomultiplier tube, and step c) comprises effecting substance analysis, color determination and contaminant detection via a processor and mathematical classification models.

11. The method of claim 10, wherein said irradiating of the substances in step a) and said detecting of said re-emitted radiation in step b) are carried out via an optical arrangement comprising a reflecting polygonal wheel and a concave toroidal mirror.

12. The method of claim 11, wherein said concave toroidal mirror comprises several individual segments.

13. A device for the examination of substance properties of a measuring material, a granulate, and tablet-like substances, the device comprising:
    a laser beam;
    an optical adjustment means for deflecting said beam and for simultaneously guiding said beam over the measuring material;
    a device for spectral decomposition of secondary radiation re-emitted by the measuring material;
    a sensor system for recording said secondary radiation, including a multi-anode photomultiplier for detecting said re-emitted secondary radiation;
    means for evaluation of received secondary radiation, including signal preparation means, programmed logic and mathematical algorithms including calibration vectors for effecting substance analysis, color determination and contaminant detection.

14. The device of claim 13, wherein said optical adjustment means comprise a reflecting polygonal wheel and a concave toroidal mirror for irradiating the measuring material and for detecting said re-emitted secondary radiation.

15. The device of claim 14, wherein said concave toroidal mirror comprises several individual segments.

16. A device for the examination of substance properties of a measuring material, a granulate, and tablet-like substances, the device comprising:
    a laser beam; an optical adjustment means for deflecting said beam and for simultaneously guiding said beam over the measuring material;
    a device for spectral decomposition of secondary radiation re-emitted by the measuring material;
    a sensor system for recording said secondary radiation, including a multi-anode photomultiplier for detecting said re-emitted secondary radiation;
    means for evaluation of received secondary radiation, including signal preparation means with analog multi-channel signal processing according to mathematical models with summing up of a contents of all signal channels and classification of a summed signal to effect substance analysis, color determination and contaminant detection.

17. The device of claim 16, wherein said optical adjustment means comprise a reflecting polygonal wheel and a concave toroidal mirror for irradiating tile substance and for detecting said re-emitted secondary radiation.

18. The device of claim 17, wherein said concave toroidal mirror comprises several individual segments.

19. A device for the examination of substance properties of a measuring material, a granulate, and tablet-like substances, the device comprising:
- a laser beam;
- an optical adjustment means for deflecting said beam and for simultaneously guiding said beam over the measuring material;
- a device for spectral decomposition of secondary radiation re-emitted by the measuring material;
- a sensor system for recording said secondary radiation, including a multi-anode photomultiplier for detecting said re-emitted secondary radiation;
- means for evaluation of received secondary radiation, including a processor having access to reference spectra contained in a data memory for effecting substance analysis, color determination and contaminant detection.

20. The device of claim 19, wherein said optical adjustment means comprises a reflecting polygonal wheel and a concave toroidal mirror for irradiating the substance and for detecting said re-emitted secondary radiation.

21. The device of claim 20, wherein said concave toroidal mirror comprises several individual segments.

22. A device for the examination of substance properties of a measuring material, a granulate, and tablet-like substances, the device comprising:
- a laser beam;
- an optical adjustment means for deflecting said beam and for simultaneously guiding said beam over the measuring material;
- a device for spectral decomposition of secondary radiation re-emitted by the measuring material;
- a sensor system for recording said secondary radiation, including a multi-anode photomultiplier for detecting said re-emitted secondary radiation;
- means for evaluation of received secondary radiation, including a processor and mathematical classification models for effecting substance analysis, color detection and contaminant detection.

23. The device of claim 22, wherein said optical adjustment means comprise a reflecting polygonal wheel and a concave toroidal mirror for irradiating the measuring material and for detecting said re-emitted secondary radiation.

24. The device of claim 23, wherein said concave toroidal mirror comprises several individual segments.

* * * * *